United States Patent
Neuberger

(10) Patent No.: US 9,681,917 B2
(45) Date of Patent: Jun. 20, 2017

(54) FIBER LASER SYSTEM FOR MEDICAL APPLICATIONS

(71) Applicant: BIOLITEC PHARMA MARKETING LTD., Labuan (MY)

(72) Inventor: Wolfgang Neuberger, Dubai (AE)

(73) Assignee: Biolitec Unternehmens Beteiligungs IIAG, Vienna (AT)

(*) Notice: Subject to any disclaimer, the term of this patent is extended or adjusted under 35 U.S.C. 154(b) by 193 days.

(21) Appl. No.: 14/397,104

(22) PCT Filed: Apr. 26, 2013

(86) PCT No.: PCT/IB2013/001118
§ 371 (c)(1),
(2) Date: Oct. 24, 2014

(87) PCT Pub. No.: WO2013/160770
PCT Pub. Date: Oct. 31, 2013

(65) Prior Publication Data
US 2015/0126982 A1    May 7, 2015

Related U.S. Application Data

(60) Provisional application No. 61/639,615, filed on Apr. 27, 2012, provisional application No. 61/716,354, filed on Oct. 19, 2012.

(51) Int. Cl.
G02B 6/028 (2006.01)
A61B 18/22 (2006.01)
(Continued)

(52) U.S. Cl.
CPC .............. *A61B 18/22* (2013.01); *G02B 1/12* (2013.01); *G02B 1/14* (2015.01); *H01S 3/067* (2013.01);
(Continued)

(58) Field of Classification Search
None
See application file for complete search history.

(56) References Cited

U.S. PATENT DOCUMENTS 6,687,445 B2 * 2/2004 Carter ............... C03B 37/01294
372/6
7,627,007 B1 * 12/2009 Armstrong ............ G02F 1/3501
372/21
(Continued)

*Primary Examiner* — Sung Pak
(74) *Attorney, Agent, or Firm* — BJ Associates; Bolesh J. Skutnik

(57) ABSTRACT

Improved/efficient fiber laser systems are provided for medical/cosmetic applications, comprising at least one pump source, optically coupled with at least one fiber laser. The fiber laser comprises an irregularly-shaped single-, double- or multiple-clad fiber of unconventional structure and geometry, and means for partially/completely reflecting the pump radiation, such as Bragg gratings. The fiber laser system further comprises at least one fiber optic delivery device optically coupled with the pump source, with the irregularly-shaped single-, double- or multiple-clad fiber laser, or with both, to convey laser radiation to a treatment site. The fiber optic delivery device comprises one or more waveguides, preferably optical fibers. The irregularly-shaped fiber laser and waveguides of the fiber optic delivery device have the same or different tip configurations to perform the treatment according to therapeutic needs. In a preferred embodiment, the fiber laser treatment system operating at 915±30 nm, 975±30 nm and/or 1550±40, comprises control means to select delivery of one, two or three output laser beams, and regulates their respective output powers.

15 Claims, 5 Drawing Sheets

(51) Int. Cl.
  *G02B 1/14* (2015.01)
  *G02B 1/12* (2006.01)
  *H01S 3/067* (2006.01)
  *G02B 6/26* (2006.01)

(52) U.S. Cl.
  CPC .. *H01S 3/06745* (2013.01); *A61B 2018/2222* (2013.01); *A61B 2018/2244* (2013.01); *A61B 2018/2277* (2013.01); *A61B 2018/2294* (2013.01); *G02B 6/262* (2013.01); *H01S 3/06729* (2013.01); *H01S 3/06733* (2013.01)

(56) References Cited

U.S. PATENT DOCUMENTS

| | | | | |
|---|---|---|---|---|
| 2003/0187325 A1* | 10/2003 | Meister | ............. | A61B 18/20 600/108 |
| 2004/0213301 A1* | 10/2004 | Sharma | ............. | A61B 18/22 372/3 |
| 2006/0024008 A1* | 2/2006 | Galvanauskas | ... | C03B 37/02745 385/123 |
| 2006/0045163 A1* | 3/2006 | Chuang | ............. | H01S 3/06754 372/100 |
| 2006/0280217 A1* | 12/2006 | Zervas | ............. | H01S 3/067 372/72 |
| 2009/0003788 A1* | 1/2009 | Galvanauskas | ... | C03B 37/02745 385/126 |
| 2010/0167226 A1* | 7/2010 | Altshuler | ............. | A61B 18/20 433/29 |
| 2010/0247047 A1* | 9/2010 | Filippov | ............. | C03B 37/02763 385/127 |
| 2011/0024927 A1* | 2/2011 | Galvanauskas | ... | C03B 37/02745 264/1.29 |
| 2011/0058250 A1* | 3/2011 | Liu | ............. | G02B 6/14 359/341.3 |
| 2011/0274129 A1* | 11/2011 | Bauer | ............. | C03B 23/207 372/39 |
| 2012/0127563 A1* | 5/2012 | Farmer | ............. | H01S 3/06754 359/341.3 |
| 2012/0219026 A1* | 8/2012 | Saracco | ............. | G02B 6/14 372/21 |
| 2012/0262781 A1* | 10/2012 | Price | ............. | G02B 6/14 359/341.3 |

\* cited by examiner

8a

8b

FIBER LASER SYSTEM FOR MEDICAL APPLICATIONS

RELATED CASE INFORMATION

This application claims the benefit of U.S. Provisional Application Ser. No. 61/639,615, filed Apr. 27, 2012, entitled "Fiber Laser System for Medical Applications" and U.S. Provisional Application Ser. No. 61/716,354, filed Oct. 19, 2012, entitled "Fiber Laser System for Medical Applications", which are incorporated by reference in its entirety herein.

BACKGROUND OF THE INVENTION

1. Field of the Invention

The present invention relates to electromagnetic radiation systems for medical or cosmetic applications, and more particularly to devices providing one or more laser radiation wavelengths for medical or cosmetic applications.

2. Invention Disclosure Statement

Laser devices have shown many advantages in comparison with other technologies for medical and cosmetic applications where light of the required spatial or temporal coherence could not be produced using simpler technologies. However, the technology has sometimes lead to expensive, heavy, bulky and complicated devices, especially when high energy or power density is required for a given medical application.

Furthermore, these laser devices can usually give only a single laser wavelength at a time when in some circumstances it would be desirable to have a more powerful laser device capable of providing more than one laser wavelength, as this offers an broader range of therapeutic effects.

Dimensionally, fiber lasers usually have sizes comparable to less than a single strand of hair. For single mode fibers, typically, the core diameter is about 8-10 microns, with an overall cladding diameter of 125 microns and then various types of jacketing material are applied for added mechanical strength protection, typically with outer diameters of 500 microns, to over a few microns for metal over-jacketed fibers.

To overcome the disadvantages of prior art laser devices for medical or cosmetic treatments, a fiber laser device for medical/cosmetic procedures by use of a tunable fiber laser is disclosed in U.S. Pat. No. 6,723,090 by Altshuler et al. The fiber laser is included in a box containing control and other electronics, a cooling mechanism, a diode laser, suitable optics and an acoustic module for tuning the wavelength of the fiber laser. Part of the fiber laser is in the box and extends through an umbilical up to a handpiece. Extreme caution has to be taken as the main component of the system, namely the fiber laser is only covered by an umbilical. Furthermore, the high power that can be achieved is limited as the length of the fiber laser is restricted to the length of the umbilical. Alternatively, all these components can be inside a handpiece, leading to a heavy and clumsy system whose weight is increased when a longer fiber laser length is desired for high energy applications.

Another example of medical laser apparatus comprising fiber lasers is disclosed in U.S. Pat. No. 7,408,963 by Hayashi at al. The medical apparatus provides visible laser beams each having a different wavelength, having an inexpensive structure. However, this medical apparatus has a limited versatility, as many prior art medical laser devices have, as its application is limited to the use of a single laser wavelength at a time and hence a limited therapeutic effect is achieved. Whereas it would be desirable to have a laser device whose laser wavelength output could be adjusted to obtain a combined therapeutic effect, controlling the degree of vaporization, coagulation and ablation, without the need to choose only a single effect. Furthermore, the invention disclosed herein is also suitable for high power applications, but the invention of Hayashi at is for applications which do not need to cope with high intensity. It is an inexpensive structure however its application is limited to the use of a lower power, single laser wavelength and hence the versatility of the system is diminished.

Thus, there is a need for a versatile, compact and lightweight laser system for medical and cosmetic applications, involving the delivery of laser energy to the tissue in an efficient manner and providing the desired therapeutic effect, wherein multiple wavelengths and high powers are desirable. Present invention addresses these needs by providing economic, versatile, safe and efficient laser systems.

OBJECTIVES AND BRIEF SUMMARY OF THE INVENTION

It is an objective of the present invention to provide a new generation of laser systems for medical and cosmetic applications comprising fiber lasers with unconventional structure and geometry.

It is also an objective of the present invention to provide laser devices that enable incision, vaporization and coagulation to be performed selectively and accurately according to therapeutic needs.

It is yet another objective of the present invention to provide fiber optic delivery devices for controlled and accurate laser energy delivery, to minimize the possibility of harming patients.

Briefly stated, the present invention provides improved/efficient fiber laser systems for medical/cosmetic applications, comprising at least one pump source, optically coupled with at least one fiber laser. The fiber laser comprises an irregularly shaped single-, double- or multiple-clad optical fiber of unconventional structure and geometry and means for partially/completely reflecting the pump radiation, such as Bragg gratings. The fiber laser system further comprises at least one fiber optic delivery device optically coupled with the pump source, with the irregularly shaped single-, double- or multiple-clad fiber, or with both, to convey laser radiation to a treatment site. The fiber optic delivery device comprises one or more waveguides, preferably optical fibers. The irregularly shaped fiber laser and the waveguides of the fiber optic delivery device have the same or different tip configurations to perform the treatment according to therapeutic needs. In a preferred embodiment, the fiber laser treatment system operates at 915±30 nm, 975±30 nm and/or 1550±40, comprises control means to select delivery of one, two or three output laser beams, and to regulate their respective output powers.

The above and other objects, features and advantages of the present invention will become apparent from the following description read in conjunction with the accompanying drawings (in which like reference numbers in different drawings designate the same elements).

DETAILED DESCRIPTION OF PREFERRED EMBODIMENTS

The invention described herein provides many advantages over prior art alternative devices and methods for medical and cosmetic applications concerning the use of laser energy. It provides simpler and more efficient methods and devices for a variety of medical and cosmetic applications including dermatology, ENT, gynecology, proctology, ophthalmology, phlebology, pneumology, gastroenterology, spinal disk surgery, thoracic surgery, general laser surgery, dental treatments and urology treatments.

This new generation of fiber laser systems enables incision, vaporization, coagulation and tissue alteration to be performed selectively and accurately according to the therapeutic needs. Another advantage of the fiber laser systems disclosed herein is the excellent pump conversion efficiency and superior beam quality of the laser light, in comparison with prior art devices, due to the use of irregularly shaped single-, double or multiple-clad fiber lasers. Furthermore, the fiber laser system combines irregularly shaped single-, double- or multiple-clad gain fibers with high power pump sources with low brightness beam, such as diode lasers, leading to a cost-effective laser system with superior output characteristics. This combination provides high power laser systems in a compact and space-saving design as well as low-maintenance and reliable laser sources.

In a preferred embodiment, a fiber laser treatment system for medical or cosmetic applications comprises at least one low-brightness pump source, and at least one fiber laser which has an irregularly shaped single-, double- or multiple-clad optical fiber and means for completely or partially reflecting pump laser radiation, such as Bragg gratings. The fiber laser system further comprises at least one fiber optic delivery device containing one or more optical fibers to convey laser radiation to a treatment site. The optical fibers within the fiber optic delivery device can have the same or different tip configuration to perform the desired coagulation, ablation or tissue alteration.

The pump source is a diode laser source; preferably a low-brightness diode laser source. Single or multiple pumping lasers may be used, depending on the laser wavelengths that will be delivered by the medical device. In one embodiment, the pump laser source (input) operates at a laser wavelength in the range of about 800 to 2100 nm, more specifically but not limited to a laser wavelength selected from the group of about 800, 850, 900-970, 980, 1047, 1068, 1470 and 1480 nm. The irregularly shaped single-, double- or multiple-clad fiber of the fiber laser system delivers laser radiation in a single mode, a near single mode, a high energy beam, a high peak energy beam, continuous mode, pulsed mode, Q-switch mode, and combinations of these.

Figure 1:
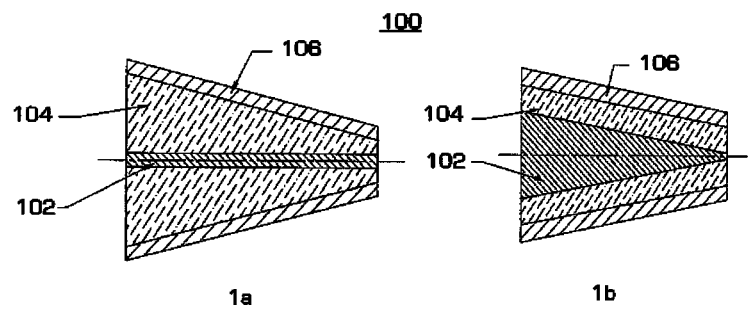
FIG. 1a shows a preferred embodiment of a section of a double-clad optical fiber of unconventional structure and geometry comprising an active core, an inner cladding and an outer cladding, wherein the active core is constant and the inner and outer cladding change gradually forming a tapered longitudinal profile, over the section of the fiber.
FIG. 1b shows a preferred embodiment of a section of an irregularly shaped double-clad optical fiber comprising an active core gradually changing forming a tapered longitudinal profile, and an inner cladding with a constant thickness over the section of the fiber.

A section of active double-clad fiber 100 with irregular structure disclosed in a preferred embodiment is shown in FIGS. 1a and b. Irregularly shaped double-clad fiber 100 mainly comprises active core 102, inner cladding 104 over active core 102, and an outer cladding 106 around inner cladding 104. Active core 102 has as an active gain medium, a core doped with rare-earth elements such as erbium, ytterbium, neodymium, dysprosium, praseodymium, and thulium, where the lasing beam propagates; and inner cladding 104 where the beam from the pump source propagates (pump core). Inner cladding 104 guides the pump laser radiation along the fiber, and the pump radiation that crosses the optical axis of the fiber where the doped core is, activates the laser wavelength within active core 102. The active gain medium of active core 102 absorbs the energy of the pump radiation, excites the atoms of the gain medium and generates a laser radiation with a wavelength different from the wavelength of the pump radiation. Inner cladding 104 contains the generated laser radiation radially within active core 104. The section of active double-clad fiber 100 is shown in FIG. 1a. The irregular geometry is characterized by active core 102 with a constant diameter and a gradually changing thickness of the inner cladding 104 and outer cladding 106, forming a tapered longitudinal profile. In another embodiment shown in FIG. 1b, the diameter of active core 102 of irregularly shaped double-clad fiber 100 changes gradually along the length of the section of the optical fiber, thus forming a tapered longitudinal profile and enabling a continuous mode conversion. However, the thickness of inner cladding 104 remains essentially constant over a subsection, or over the entire length of the fiber. One advantage found in these configurations is that the fiber can be pumped from both ends, having a better coupling with the pump source.

Figure 2A:
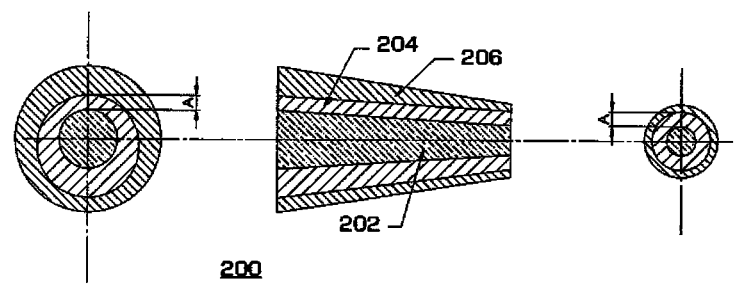
FIG. 2a shows another preferred embodiment of an irregularly shaped double-clad optical fiber which varies the eccentricity of active core along the length of the fiber by gradually changing the diameter of the active core and the thickness of a portion of the inner cladding forming a tapered longitudinal profile, while keeping constant another portion of the thickness of the inner cladding.
Figure 2B:
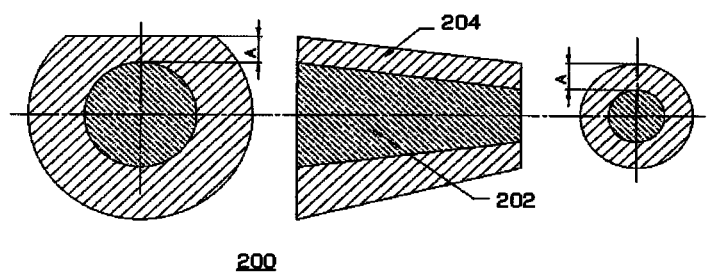
FIG. 2b shows another preferred embodiment of a section of an irregularly shaped double-clad optical fiber with a "D"-shaped profile and an off-axis active core along the length of the fiber.

In other embodiments of the irregularly shaped double-clad fiber, the shape of the inner cladding and the relative position of the active core within the inner cladding are constructed to provide an asymmetric design and a chaotic trajectory of the radiation in order to enhance the absorption of the pump radiation in the fiber. Preferably, the inner cladding is non-circular, i.e. octagonal or varying in shape over the length of the active core, and may vary its eccentricity along the length of the active core. In one embodiment shown in FIG. 2a, irregularly shaped double-clad fiber 200 is a tapered fiber with eccentric inner clad 208 on the larger side of the fiber and a centric round core-clad 210 on the smaller side of the fiber. This geometry and structure is obtained by gradually changing the diameter of active core 202 along the length of the optical fiber, keeping constant a portion of the thickness of inner cladding 204 and gradually changing the thickness of the other portion of inner cladding 204. The side view of this embodiment, depicted in FIG. 2a, shows that by keeping constant the thickness of inner cladding 204 in the upper section and gradually changing the thickness of the lower section of inner cladding 204, active core 202 is off-axis on the large side of the fiber. In another embodiment shown in FIG. 2b, irregularly shaped double-clad fiber 200 has a constant thickness in a portion of inner cladding 204 and a gradually changing thickness in another portion of inner cladding 204, but also a "D"-shaped profile leading to an off-axis active core 202 on the large side of irregularly shaped double-clad fiber 200.

Additionally, the irregularly shaped double-clad fiber typically has one or more regions for reflecting particular wavelengths of light and transmitting others such as a distributed Bragg reflector constructed in a short segment of optical fiber, known as fiber Bragg grating. In one embodiment, fiber Bragg gratings having a periodic variation in the refractive index of the fiber core and generating a wavelength specific dielectric mirror, are used for blocking certain wavelengths or as a wavelength-specific reflector. The basic physics behind this behavior is known in the prior art.

Figure 3:
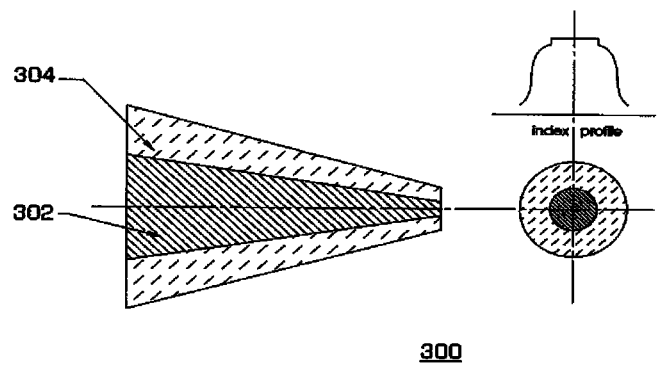
FIG. 3 shows another preferred embodiment of a section of an active optical fiber comprising an inner cladding and an active core, wherein the inner cladding is a graded-index cladding with a refractive index that varies with increasing radial distance from the fiber axis, and wherein the diameter of the active core and the thickness of the inner cladding change gradually along the length of the section of the active optical fiber forming a tapered longitudinal profile.

In another embodiment shown in FIG. 3, a section of an irregularly shaped single-clad active optical fiber 300 mainly comprises active core 302, and inner cladding 304 over active core 302. The diameter of active core 302 and the thickness of inner cladding 304 change gradually along the length of the section of active optical fiber forming a tapered longitudinal profile. Inner cladding 304 is a graded-index cladding with a refractive index that varies with increasing radial distance from the fiber axis. The preferred material composition of the inner cladding is fluorine doped silica.

Figure 4:
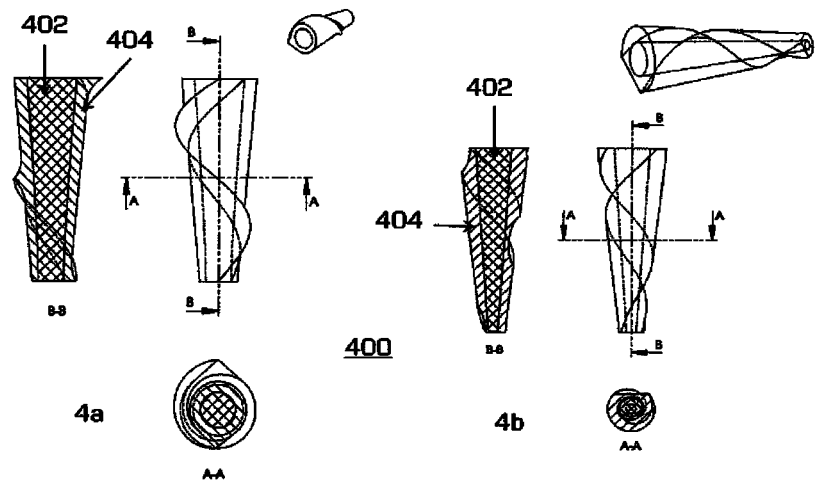
FIG. 4a depicts a preferred embodiment of present invention showing an active optical fiber having one edge shape profile, a gradually changing active core diameter and inner cladding thickness forming a tapered longitudinal profile, while at the same time having a twisted shape over the length of the fiber, exhibiting a non-continuous change in clad thickness.
FIG. 4b depicts a preferred embodiment of present invention showing an active optical fiber having one "D" shape profile, a gradually changing active core diameter and inner cladding thickness forming a tapered longitudinal profile, and a twisted shape over the length of the fiber, leading to an off-axis active core along the length of said fiber.

In another embodiment shown in FIG. 4a, irregularly shaped double-clad fiber 400 has a helically ridged tapered profile and comprises active core 402, inner cladding 404 and outer cladding (not shown), wherein the diameter of active core 402 and the thickness of inner cladding 404 change gradually forming a tapered longitudinal profile while at the same time are twisted over the length of the fiber, exhibiting a non-continuous change in clad thickness. Preferably octagonal or other non-round shapes are used for active core 402 and inner cladding 404 as asymmetric designs cause a chaotic trajectory of the radiation and enhances the absorption of the pump radiation in the fiber. Another embodiment in FIG. 4b, shows irregularly shaped double-clad fiber 400 with a "D" shape profile wherein inner cladding 404 changes in a non gradual manner.

Figure 5:
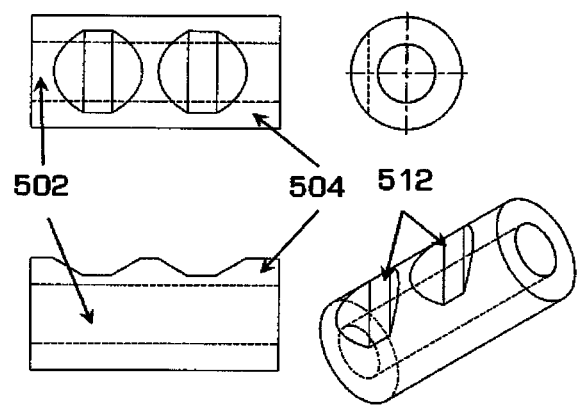
FIG. 5 shows an embodiment of a preform having an inner cladding of constant thickness on one side and cleavages on another side, for manufacturing irregular tapered fibers with a "D"-shaped profile.

In one embodiment, a method of manufacturing irregularly shaped double-clad fibers with irregularly shaped longitudinal profiles as shown in FIG. 1-4 comprises the steps of 1) manufacturing the preform by methods known in the state of the art, wherein an adequate forming of preform geometry in longitudinal direction for every piece of the irregularly shaped fiber is necessary; and 2) drawing the perform. The precise profile parameters with reproducible results are achieved using an external cylindrical grinding machine with software option for unrounded cross sections. During the drawing of the optical fiber, the synchronization of the different drawing parameters such as preform position, take-off preform speed, diameters, and take-up fiber speed, are controlled with programmable logic controllers (PLC) for obtaining precise longitudinal tapered fiber profiles. FIG. 5 shows an example of a preform for manufacturing irregularly shaped fibers having a tapered longitudinal profile and an irregular shape such as that shown in FIG. 2b. In one embodiment, a section of a perform for obtaining an irregularly shaped double-clad fiber with a constant thickness in a portion of inner cladding and a gradually changing thickness in another portion of inner cladding with a "D"-shaped profile (FIG. 2b) is shown in FIG. 5 and comprises inner cladding 504 of constant thickness on one side of the optical fiber, active core 502, and cuts 512 in another portion of inner cladding 504.

In another embodiment, a method of manufacturing the irregularly shaped double-clad fiber comprises the steps of 1) manufacturing the preform by methods known in the state of the art, such as modified chemical vapor deposition or outside vapor deposition, 2) drawing the perform in a furnace; 3) removing by etching or laser ablation, part of the inner cladding on the draw tower, after the draw furnace; 4) coating the optical fiber with silicone or hard clad, as outer cladding; and 5) winding on a drum.

In another embodiment, a method of manufacturing the irregular active core of the irregularly shaped double-clad fiber laser includes the step of varying the amount of material deposited on the outer core area of the active core by removing part of the material by selectively etching some material away after deposition or by etching or laser ablating part of the inner cladding on the draw tower, after the draw furnace and before a coating is applied.

Figure 6:
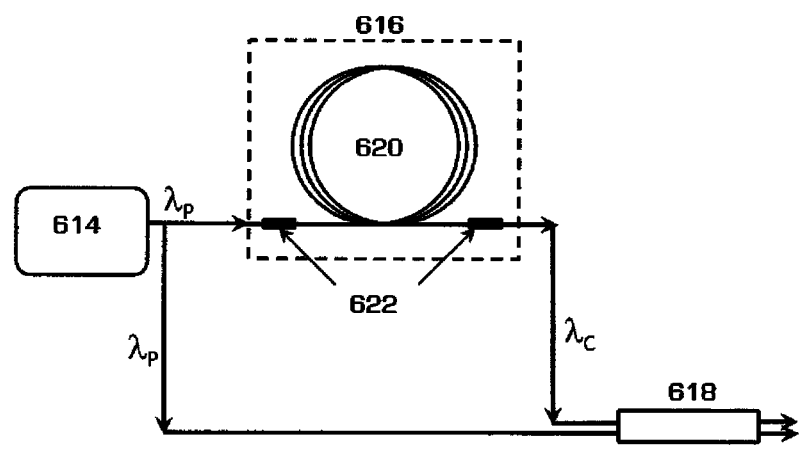
FIG. 6 depicts a preferred embodiment of present invention illustrating a fiber laser system device for medical and cosmetic applications comprising a low-brightness pump source, one fiber laser with a double-clad fiber of unconventional structure and geometry and a fiber optic delivery device.

In an embodiment, depicted in FIG. 6, low-brightness pump source 614 is optically coupled to fiber laser 616 and fiber optic delivery device 618. Fiber laser 616 comprises irregularly shaped single- or double-clad optical fiber 620 such as the ones disclosed in previous embodiments, with means 622 at the narrow-core end and at the wide-core end for partially or completely reflecting the pump laser radiation. Low-brightness pump source 614 emits pump laser radiation of wavelength $\lambda_P$, part of which pumps the active core of the fiber laser 616 and part of which is directed to treatment site with the aid of fiber optic delivery device 618. The pump laser light $\lambda_P$ is reflected in the doped fiber section of fiber laser 616 wherein the laser light $\lambda_C$ is generated and enhanced. The output of fiber laser 616, $\lambda_C$, is delivered to tissue with the aid of fiber optic delivery device 618. Both laser radiation of wavelength $\lambda_P$ and $\lambda_C$, are delivered by fiber optic delivery device 618 to treatment site. In this embodiment, the fiber optic delivery device/component comprises a single optical fiber that conveys laser radiation to a preselected treatment site, determined in accordance with the therapeutic needs. Preferably, the fiber optic delivery device is an double-clad optical fiber which can have different distal tip shapes, including a single or multi-radial tip, a twister tip, a side emitting tip, a bare tip, an off-axis tip, a double core tip, a flat tip, a fat tip, a conical tip, a tip with inversely tapered ends, a Bragg grating for beam shaping at or near the tip, scraper tips, among others. Hence, the laser treatment system of this embodiment delivers two laser radiations $\lambda_P$ and $\lambda_C$ to treatment site with the aid of a double-clad or single clad optical fiber with a tip shape that depends on the treatment site and therapeutic needs.

Figure 7:
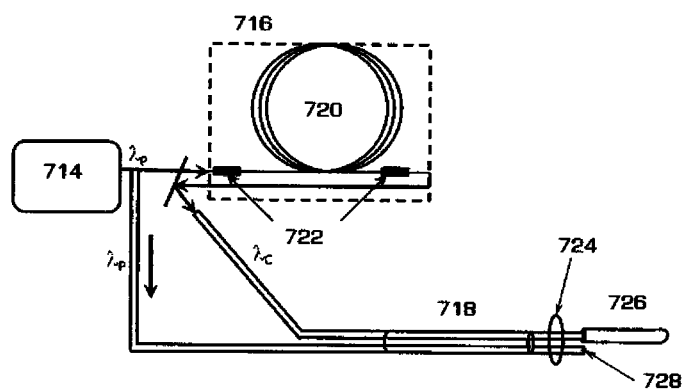
FIG. 7 depicts another preferred embodiment of present invention illustrating a fiber laser system device for medical and cosmetic applications using a diode laser, one irregularly shaped double-clad fiber laser and a fiber optic delivery device with radial and flat tip configurations.

In another embodiment shown in FIG. 7, low brightness pump source 714 operates at a laser radiation wavelength of about 975 nm and is optically coupled to fiber laser 716 which comprises irregularly shaped single- or double-clad optical fiber 720 such as the ones disclosed in previous embodiments with Brag gratings 722; and fiber optic delivery device 718. Fiber laser 716 generates a laser radiation of about 1550 nm. Fiber optic delivery device 718 comprises two waveguides 724, preferably optical fibers, with two tips for delivering laser radiation to treatment site. Radial tip 726 is optically coupled with fiber laser 716 and delivers the laser radiation of about 1550 nm whereas flat tip 728 is optically coupled with low brightness pump source 714 and delivers the laser radiation of about 975 nm.

Figure 8:
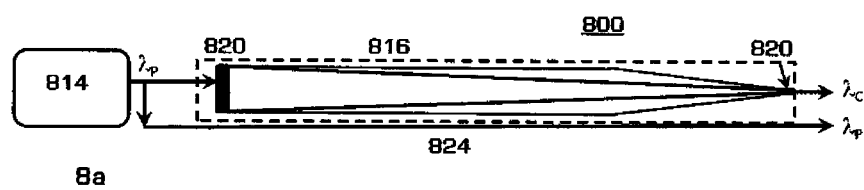
FIG. 8a shows another preferred embodiment of present invention comprising a low brightness pump source and an irregularly shaped double-clad fiber laser. One laser radiation is delivered directly from the pump source and the other from the narrow-core end of the irregularly shaped double-clad fiber laser.
FIG. 8b shows another preferred embodiment of present invention comprising a low brightness pump source, an irregularly shaped double-clad fiber laser and a fiber optic delivery device for conveying both laser radiations to treatment site.
Figure 8:
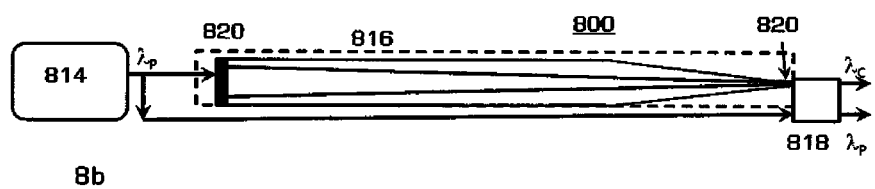

FIG. 8a shows another embodiment, wherein the fiber laser treatment system delivers two laser radiations to treatment site, one directly from a pump laser source, $\lambda_P$, and the other directly from a fiber laser, $\lambda_C$. Fiber laser treatment system 800 comprises low brightness pump source 814 optically coupled to fiber laser 816 having Bragg gratings 820. Part of the pump laser radiation, $\lambda_P$, is delivered directly to treatment site with the aid of waveguide 824 and part of the pump laser radiation, $\lambda_P$, is guided through inner cladding of fiber laser 816 for pumping the laser wavelength $\lambda_C$. The laser wavelength $\lambda_C$ is then delivered to treatment site directly though the tip of fiber laser 816. Fiber laser 816 is flexible and has a diameter smaller than 125 μm. In one embodiment, this small diameter is obtained by having a thin cladding and/or substantially thinner coatings over all, or part of its length.

In another embodiment shown in FIG. 8b, instead of a waveguide and the fiber laser, the laser radiations $\lambda_P$ and $\lambda_C$ are delivered together to treatment site with the aid of fiber optic delivery device 818, comprising two optical fibers. These optical fibers can have the same or different tip configuration depending on the radiation wavelength, treatment site and therapeutic needs.

An additional beneficial characteristic of the fiber laser comprising the irregularly shaped single-, double- or multiple-clad fibers is its versatility when it is used for delivering laser radiation directly to treatment site/tissue. In one embodiment, the irregularly shaped fiber laser is flexible and has a small diameter of less than 125 μm, so as to enable insertion or virtually atraumatic insertion into tissue. These characteristics allow for a more accurate laser energy delivery in a predetermined treatment area, minimizing the risks of involuntary irradiating healthy tissue surrounding the target.

In another embodiment, the fiber laser has a total diameter sufficiently larger than 125 μm, to provide a predetermined rigidity, stiffness and durability, which is lacking in thin fibers, but is desired for many medical treatments. These features are obtained by enlarging the clad diameter, enlarging the coatings or adding different coatings over at least part or all of the active core's length.

Figure 9A:
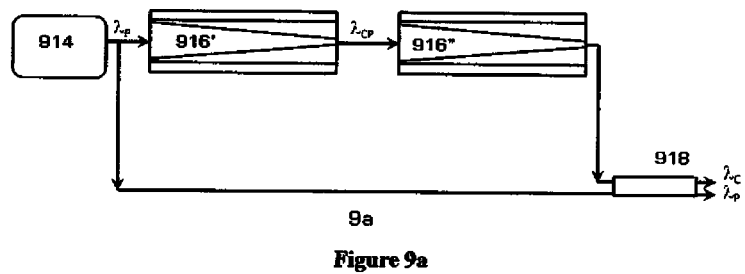
FIG. 9a shows another preferred embodiment of present invention comprising a pump source, two irregularly shaped double-clad fiber lasers and a fiber optic delivery device for conveying two laser radiations to treatment site.

In order to increase the final output power of the fiber laser system for medical applications such as lithotripsy and hard or soft tissue removal, two or more fiber lasers can be coupled in series or in parallel, giving a great potential for power scaling, according to the therapeutic needs. In the embodiment, shown in FIG. 9a, pump source 914 delivers part of its output radiation $\lambda_P$ directly to tissue with the aid of fiber optic delivery device 918, and part of its output radiation $\lambda_P$ to irregularly shaped double-clad fiber laser 916'. The active core of irregularly shaped double-clad fiber laser 916' generates laser light $\lambda_{CP}$ which is used for pumping irregularly shaped double-clad fiber laser 916". Irregularly shaped double-clad fiber laser 916" absorbs the radiation $\lambda_{CP}$ in its doped fiber section and generates laser light $\lambda_C$ which is directed to tissue with the aid of fiber optic delivery device 918. In this embodiment, fiber optic delivery device 918 comprises a single double-clad optical fiber which simultaneously delivers two laser radiations, namely $\lambda_P$ and $\lambda_C$.

Figure 9B:
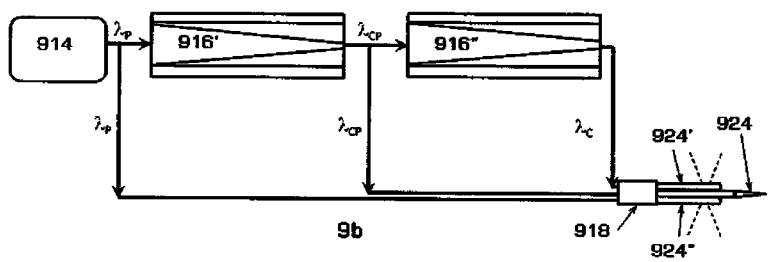
FIG. 9b shows another preferred embodiment of present invention comprising a pump source, two irregularly shaped double-clad fiber lasers and a fiber optic delivery device for conveying three laser radiations to treatment site.

FIG. 9b shows another embodiment wherein three laser wavelengths are delivered to treatment site, i.e. $\lambda_P$, $\lambda_{CP}$ and $\lambda_C$, with the aid of fiber optic delivery device 918. Fiber optic delivery device 918 comprises three separate waveguides, preferably optical fibers in order to perform a desired treatment. In this embodiment, optical fibers 924' and 924" have a side emitting tip and optical fiber 924 has a conical tip.

By choosing the appropriate combination of wavelengths and settings according to the therapeutic needs, the fiber laser system of this invention selectively and accurately performs incision, vaporization and/or coagulation. Thus, a combined, enhanced and efficient therapeutic effect by using different laser wavelengths in a single treatment can be obtained. The different degrees of incision, vaporization and/or coagulation are determined by the diverse combinations of laser wavelengths and settings. In a preferred embodiment, $\lambda_P$ is about 980±30 nm and $\lambda_C$ is in the range of 1510 to 1590 nm, preferably, about 1550 nm. The main advantage of this configuration is the possibility to obtain a combined therapeutic effect, namely coagulation and ablation, in a compact, safe, efficient and inexpensive device. This fiber laser system can provide high-energy beams for prostate tissue removal treatments wherein coagulative and ablative therapeutic effects can be obtained with the same system, as the laser wavelengths of 980 and 1550 nm are highly absorbed by hemoglobin and by water respectively. In another embodiment, $\lambda_P$ is about 1470±40 nm and $\lambda_C$ is in the range of 1510 to 1590 nm, preferably, about 1550 nm. In this case an enhanced ablation is obtained due to the delivery of a laser light of different wavelengths to the tissue, which due to its heterogeneous structure can usually have different laser absorption properties. Additionally, the combination of these wavelengths provides an improved beam power density. In other embodiments, the fiber laser system for medical or cosmetic applications delivers laser radiation either from one or more fiber lasers and/or from the pump source and operates at one or more laser wavelengths selected from the group of 915, 975, 980, 1030, 1320, 1470, 1550, 1900, 2000, 2100 nm, for different medical applications. In one embodiment, the fiber laser system for medical/cosmetic treatments operates at a laser wavelength around 1900 to 2100 nm, and around 1320 or 1470 to 1550 nm for those applications which require high absorption by water.

In another preferred embodiment, the diode laser delivers a laser radiation ($\lambda_P$) of about 915 nm, part of which is delivered directly to the tissue to be treated and part pumps a first irregularly shaped double-clad fiber laser. This first irregularly shaped double-clad fiber laser emits a laser radiation ($\lambda_{CP}$) of about 975 nm which pumps a second irregularly shaped double-clad fiber laser. This second irregularly shaped double-clad fiber laser delivers a laser radiation to the tissue with a laser wavelength ($\lambda_C$) of about 1550±40 nm. Thus, the tissue receives two laser wavelengths, namely about 915 nm and about 1550 nm. The main advantage over prior art devices is the possibility to deliver a combined laser emission for medical applications in order to achieve different therapeutic effects from the two wavelengths in a single procedure. Furthermore, the capability of using the small irregular end as the emission surface permits higher power density and beam quality to be delivered to tissue, thus allowing a greatly enhanced laser energy treatment.

In some treatments, during a procedure, only a single laser wavelength is desired for a certain stage of a treatment. The fiber laser system of the present invention permits generating and delivering a single laser wavelength, or a combined set of laser wavelengths, according to the therapeutic effect required in each stage of the medical procedure. For operating at a single wavelength, the fiber laser treatment system has a control module which is used to select which wavelength is going to be delivered and which are going to be momentarily blocked. Additionally, the fiber laser treatment system can operate at one or more laser wavelengths but with different output power. In this case, the control module manages the output power of the different laser wavelengths of the laser treatment system. In one embodiment of a fiber laser system operating at 980±30 nm (pump laser source) and 1550±40 nm (fiber laser), when the procedure requires a coagulation effect, the laser system blocks the output of the fiber laser and the treatment beam only comprises the laser radiation delivered by the pump laser source. Proceeding further with the procedure, the physician requires a simultaneous ablation and coagulation effect for tissue removal in a highly irrigated area. Hence, the fiber laser system delivers both laser wavelengths together and the treatment beam comprises the light emitted by the pump laser source and by the fiber laser.

The present invention is further illustrated by the following examples, but is not limited thereby.

Example 1

A fiber laser system for endovascular applications operating at laser wavelengths of about 980 nm and of about 1550 nm is hereby exemplified. The laser system has a diode laser, emitting laser radiation of 980±30 nm, which acts as a pumping source for an erbium-doped, irregularly shaped double-clad fiber laser core. The fiber laser component of the fiber laser system emits a laser radiation of 1550±40 nm. Both wavelengths are delivered together using optical fibers. The laser radiation of 1550±40 nm is delivered with the aid of an optical fiber with a radial emitting tip which is optically coupled to the irregularly shaped double-clad fiber laser source, and the laser radiation of 980±30 nm is delivered with the aid of an optical fiber with a flat tip which is optically coupled to the diode laser. The emitting tips of the radial and flat fibers are placed inside a greater saphenous vein, typically with the aid of introducing means such as a needle, a guide wire and/or a catheter. In this example, after inserting the needle, a catheter was introduced inside the vein, the needle was removed, then a guide wire was introduced through the vein to be treated, and afterwards the optical fibers were introduced until their tips reached the position to start the treatment. Once the distal ends of the fibers were in position, the catheter and the guide wire were withdrawn, leaving the optical fibers in place. These initial steps were performed under ultrasound guidance. Then, laser energy was delivered to the inside of the vein while withdrawing the optical fibers, leading to the vein's closure along the treated length.

Example 2

A fiber laser system for lithotripsy treatments operating at laser wavelengths of about 1950±50 nm is described in this example. The fiber laser system has a diode laser which acts as a pumping source, emitting laser radiation of about 975 nm. The irregularly shaped fiber laser component of the laser system emits laser radiation of about 1950±50 nm after absorption of the pumped laser radiation of 975 nm. Both laser beams are delivered together through a 400 μm optical fiber with a flat tip, which is coupled, at its proximal end to the fiber laser source. Laser light of 1950±50 nm is delivered in pulses with pulse width in the range of 100-700 μs, a repetition rate in the range of 5-25 Hz and a pulse energy in the range of 400-2000 mJ in order to focus high intensity energy and convert it into mechanical energy provoking cavitation bubbles that break, destroy or reduce the size of any calcium oxalate, uric acid and cystine urinary stones (calculi) present. The mechanical energy generated by absorption of the high-energy combined laser light is responsible for the destruction of calculi. To enhance the power of this system, a Q-switched irregularly shaped ytterbium-doped fiber laser can be used as the fiber laser component.

Example 3

Figure 10:
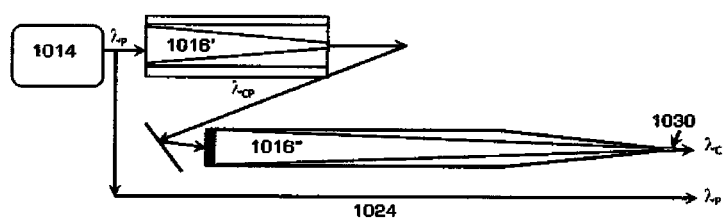
FIG. 10 shows another preferred embodiment of present invention for hard or soft tissue removal comprising a diode laser, a first irregularly shaped double-clad fiber laser optically coupled with the diode laser and a second irregularly shaped double-clad fiber laser with conical tip. The tissue receives two laser wavelengths, one from the diode laser and the other from the second irregularly shaped double-clad fiber laser with conical tip.

A fiber laser system for hard or soft tissue removal depicted in FIG. 10, comprises diode laser 1014, irregularly shaped double-clad fiber laser 1016', irregularly shaped double-clad fiber laser 1016" with conical tip 1030 and optical fiber 1024. Diode laser 1014 delivers a laser radiation ($\lambda_P$) of about 915 nm, part of which is delivered directly to the tissue to be treated with the aid of optical fiber 1024 and part of it pumps irregularly shaped double-clad fiber laser 1016'. Irregularly shaped double-clad fiber laser 1016' emits a laser radiation ($\lambda_{CP}$) of about 975 nm which pumps irregularly shaped double-clad fiber laser 1016" with conical tip 1030. Irregularly shaped double-clad fiber laser 1016" with conical tip 1030 delivers a laser radiation to the tissue with a laser wavelength ($\lambda_C$) preferably, about 1550±40 nm. Thus, the tissue receives two laser beams, namely at about 915 nm and at about 1550 nm. For Benign Prostatic Hyperplasia treatments, the laser output power of this fiber laser system is in the range of 50-60 W, in continuous mode.

Example 4

Figure 11:
FIG. 11 shows another preferred embodiment of present invention comprising a low-brightness diode laser, an irregularly shaped double-clad fiber laser with a smaller diameter than standard fibers and a twister tip configuration. Both laser wavelengths are delivered together into the twister tip and onto treatment site.

A fiber laser system for medical applications depicted in FIG. 11, uses low-brightness diode laser 1114 operating at about 915 nm, and pumps irregularly shaped double-clad fiber laser 1116 which generates a laser wavelength of about 975 nm. Irregularly shaped double-clad fiber laser 1116 has a smaller diameter of less than 125 μm, so as to enable insertion or virtually atraumatic insertion into tissue. Both laser wavelengths, i.e. 915 nm and 975 nm are delivered together to treatment site through irregularly shaped double-clad fiber laser 1116 having twister tip 1132.

Example 5

A fiber laser system for dermatological applications such as for non-ablative fractional laser skin treatments comprises a diode laser pumping an irregularly shaped Er fiber laser which generates a pulsed laser wavelength of about 1550 nm. The fiber laser system delivers a pulsed beam with pulse energy of about 1000 mJ, a pulse width of between about 10-15 ms and a repetition rate of about 2 Hz. Alternatively, the fiber laser system has a pulse output with pulse energy in the range of about 10 mJ, a pulse width of about 1 ms and a repetition rate between about 100-1000 Hz.

Example 6

A femtosecond fiber laser system for dental applications such as for caries ablation treatments comprises a diode laser pumping an irregularly shaped Yb ps-short pulse fiber laser which generates a laser wavelength of about 1030 nm. The fiber laser system delivers a pulsed beam with pulse energy of about 80 μJ, a pulse width of about 950 fs and a repetition rate of about 40 kHz and a spot diameter of 70 μs.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A fiber laser system for medical and cosmetic applications comprising,
    a low brightness diode laser pump source emitting radiation at a wavelength of $\lambda_p$;
    a fiber laser comprising an active double-clad optical fiber with an irregular structure having a receiving end and an emitting end and being optically coupled at the receiving end with said pump source;
    a first fiber optic delivery device optically coupled with said pump source and configured to deliver radiation at a wavelength of $\lambda_p$
    a second fiber optic delivery device optically coupled with the emitting end of said fiber laser and configured to deliver radiation at a wavelength of $\lambda_c$
    wherein said first and second fiber optic delivery devices comprises at least one waveguide to convey laser radiation of wavelengths of both $\lambda_p$ and $\lambda_c$ simultaneously to a treatment site.

2. The fiber laser system according to claim 1 wherein $\lambda_p$ is 980±30 nm and $\lambda_c$ is selected from 1550±40 nm and 1950±50 nm.

3. The fiber laser system according to claim 1 wherein $\lambda_p$ is 980±30 nm and $\lambda_c$ is 1550±40 nm.

4. The fiber laser system according to claim 2
    wherein said fiber optic delivery device optically coupled with said pump source and said fiber optic delivery device optically coupled with said fiber laser are a single optical fiber delivering radiation at wavelengths of 980±30 nm and 1950±50 nm;
    wherein said radiation of wavelength 1950±50 nm is delivered in pulses with pulse width of 100-700 μs, a repetition rate of 5-25 Hz, and a pulse energy of 400-2000 mJ.

5. The fiber laser system according to claim 1, wherein said fiber laser comprises a double-clad optical fiber with an active core, an inner cladding, an outer cladding, and said irregular structure is obtained over a subsection or over the entire length of said fiber by keeping constant the diameter of said active core, by keeping constant the thickness of said inner cladding, by changing gradually the diameter of said active core forming a tapered longitudinal profile, by changing gradually the thickness of said inner cladding forming a tapered longitudinal profile, or by a combination of these.

6. The fiber laser system according to claim 5, wherein the shape of said inner cladding and said active core, and the relative position of said active core within said inner cladding are constructed to provide an asymmetric design and a chaotic trajectory of radiation in order to enhance absorption of the pump radiation in the fiber laser.

7. The fiber laser system according to claim 1, wherein said double-clad optical fiber varies the eccentricity of said active core along the length of said fiber by gradually changing the diameter of said active core and the thickness of a portion of said inner cladding forming a tapered longitudinal profile, while keeping constant another portion of the thickness of said inner cladding.

8. The fiber laser system according to claim 7, wherein said double-clad optical fiber further comprises a "D"-shaped profile leading to an off-axis active core along the length of said fiber.

9. The fiber laser system according to claim 1, wherein said double-clad optical fiber laser has a tip configuration at its narrow-core end selected from the group consisting of single or multi-radial tips, twister tips, side emitting tips, bare tips, off-axis tips, double core tips, flat tips, fat tips, scraper tips, conical tips, a tip with inversely irregular ends, and a Bragg grating for beam shaping at or near the tip.

10. The fiber laser system according to claim 1, which further comprises at each of the receiving end and the emitting end of the fiber laser a means for partially reflecting the radiation emitted by the pump source.

11. The fiber laser system according to claim 10 wherein the means for partially reflecting the radiation emitted by the pump source is a Bragg grating.

12. A fiber laser system for medical and cosmetic applications comprising,
- a low brightness diode laser pump source emitting radiation at a wavelength of $\lambda_p$;
- a first fiber laser optically coupled with said pump source to receive radiation at wavelength $\lambda_p$ and deliver radiation at wavelength $\lambda_{cp}$;
- a second fiber laser optically coupled with said first fiber laser to receive radiation at wavelength $\lambda_{cp}$ and deliver wavelength at $\lambda_c$;
- a first fiber optic delivery device optically coupled with said pump source and configured to deliver radiation at wavelength $\lambda_p$
- a second fiber optic delivery device optically coupled with said second fiber laser and configured to deliver radiation at a wavelength $\lambda_c$;
- wherein said first and second fiber optic delivery devices are configured to simultaneously deliver laser radiation of both $\lambda_c$ and $\lambda_p$ to a treatment site; and
- wherein said first fiber laser and said second fiber laser each comprises a gradually tapering core that decreases in the direction away from said pump source, a first clad gradually increasing in the direction away from the pump source, and a second clad of uniform thickness.

13. The fiber laser system of claim 12 which further comprises a third optical fiber delivery device optically coupled to said first fiber laser and configured to receive radiation at wavelength $\lambda_{cp}$ and deliver said radiation to a treatment site simultaneously with the radiation of wavelengths $\lambda_c$ and $\lambda_p$.

14. The fiber laser system according to claim 12 wherein said pump source operates at one or more laser wavelengths in the range of 800 to 1480 nm.

15. The fiber laser system according to claim 14 wherein said pump source operates at one or more laser wavelengths in the range of 915 to 1480 nm.

* * * * *